US00PP20927P2

(12) United States Plant Patent
Giesen

(10) Patent No.: US PP20,927 P2
(45) Date of Patent: Apr. 13, 2010

(54) *NEMESIA* PLANT NAMED 'CNEM BULE'

(50) Latin Name: *Nemesia fruticosa, syn. N. fruticans*
Varietal Denomination: Cnem Bule

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/291,203

(22) Filed: Nov. 7, 2008

(51) Int. Cl.
*A01H 5/00* (2006.01)

(52) U.S. Cl. ..... Plt./458

(58) Field of Classification Search ..... Plt./458
See application file for complete search history.

*Primary Examiner*—Annette H Para
*Assistant Examiner*—Louanne C Krawczewicz Myers
(74) *Attorney, Agent, or Firm*—S. Matthew Edwards

(57) ABSTRACT

A new *Nemesia* plant named 'Cnem Bule', particularly distinguished by the purple-violet flowers, a relatively compact growth habit that is semi-spreading and mounding, strong stems, full well branched plant with medium-green foliage, good floriferiousness, and a slightly sweet fragrance.

1 Drawing Sheet

Latin name of the genus and species of the plant claimed: *Nemesia fruticosa, syn. N. fruticans.*

Varietal denomination: 'Cnem Bule'.

BACKGROUND OF THE NEW PLANT

The present invention comprises a new *Nemesia*, botanically known as *Nemesia fruticosa* and hereinafter referred to by the variety name 'Cnem Bule'.

'Cnem Bule' is a product of a planned breeding program. The new cultivar 'Cnem Bule' has purple-violet flowers, a relatively compact growth habit that is semi-spreading and mounded, strong stems, full well branched plant with medium-green foliage, good floriferiousness, and a slightly sweet fragrance.

'Cnem Bule' originated from a hybridization in a controlled breeding program in Andijk, Netherlands. The female parent was an unpatented hybrid seedling identified as 'NE04-71-4' with lavender color. 'NE04-71-4' has smaller flowers, lighter foliage, and shorter stems than 'Cnem Bule'.

The male parent of 'Cnem Bule' was an unpatented hybrid seedling identified as 'NE04-2-2' with blue color. 'NE04-2-2' has larger foliage, a lighter blue color, and a more spreading habit than 'Cnem Bule'.

'Cnem Bule' was selected as one flowering plant within the progeny of the stated cross in June 2005 in a controlled environment in Andijk, Netherlands. The pollination took place in October 2005 and the seed sowing in January 2006.

The first act of asexual reproduction of 'Cnem Bule' was accomplished when vegetative cuttings were propagated from the initial selection in January 2006 in a controlled environment in Andijk, Netherlands.

Horticultural examination of plants grown from cuttings of the plant initiated in January 2006 in Andijk, Netherlands, and continuing thereafter, has demonstrated that the combination of characteristics as herein disclosed for 'Cnem Bule' are firmly fixed and are retained through successive generations of asexual reproduction.

'Cnem Bule' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cnem Bule' has not been made publicly available more than one year prior to the filing of this application.

DESCRIPTION OF THE DRAWINGS

The accompanying photographic drawing shows typical flower and foliage characteristics of 'Cnem Bule' with colors being as true as possible with an illustration of this type. The photographic drawing shows 2 flowering potted plants of the new variety in a gallon pot, and a close-up of the flowers. Both of the photographs were taken in April 2008 in Gilroy, Calif. USA. Both were grown in Gilroy, Calif. USA and were approximately 4–5 months old.

DETAILED BOTANICAL DESCRIPTION

The measurements were taken on May 27, 2008 on plants that were growing in 12 cm plastic pots. Culture of these plants started around Feb. 1, 2008 in Hillscheid, Germany. The plants were nearly 4 months old.

Color Chart used: Royal Horticultural Society Colour Chart (R.H.S.) 2001

BRIEF SUMMARY OF INVENTION

The following observations, measurements, and comparisons describe plants grown outside in Hillscheid, Germany. The following traits have been repeatedly observed and are determined to be basic characteristics of the new variety. The combination of these characteristics distinguishes this *Nemesia* as a new and distinct variety.

TABLE 1

DIFFERENCES BETWEEN THE NEW VARIETY 'CNEM BULE' AND A SIMILAR VARIETY

| | 'Cnem Bule' | 'Nemhabar' (U.S. Plant Pat. No. 16,512) |
|---|---|---|
| Flower size | Larger | Smaller |
| Plant habit | More trailing | Less trailing |
| Flower color | Darker | Lighter |

Plant:

*Form, growth and habit.*—Relatively compact, semi-spreading, mounded, and well branched plant.
*Plant height.*—18–20 cm.
*Plant height (inflorescence included).*—25–32 cm.
*Plant width.*—35–40 cm.

Foliage:

*Arrangement.*—Single, opposite.
*Immature, leaf color, upper surface.*—Closest to RHS 143A.
*Lower surface.*—RHS 138B.
*Mature, leaf color, upper surface.*—RHS 137D.
*Lower surface.*—RHS 138B.
*Length.*—3–4 cm.
*Width.*—0.9–1.7 cm.
*Shape.*—Lanceolate to narrowly deltoid.
*Base shape.*—Acute to shortly attenuate.
*Apex shape.*—Acute.
*Margin.*—Serrulate.
*Texture.*—Glabrous.
*Color of veins, upper surface.*—Indistinct.
*Color of veins, lower surface.*—RHS 144B.
*Leaf venation pattern.*—Intermediate between pinnate and parallel, that is: most side veins, but not all, branch at the base and run parallel.
*Color of petioles.*—RHS144A.
*Length of petioles.*—0.1–0.3 cm.
*Width of petioles.*—0.2 cm.
*Texture of petioles.*—Glabrous.

Stem:

*Color of stem.*—RHS 143B with no anthocyanins.
*Length of stem.*—14–18 cm.
*Diameter.*—2–2.5 cm.
*Length of internodes.*—2.5–3.5 cm.
*Texture.*—Glabrous with very short and fine pubescence.

Inflorescence:

*Type.*—Terminal (located at the end shoots) raceme with flowers in an alternate, and sometimes opposite arrangement. Most often only one inflorescence at the end of a flowering stem.
*Flowering time.*—From late spring through early fall, and into fall in sheltered places.
*Inflorescence length.*—About 10–14 cm.
*Inflorescence width.*—About 2.5–3 cm.
*Number of flowers.*—12–15, of which 5–7 flowers are open at the same time.
*Quantity of inflorescences per plant.*—65–75.
*Lastingness of individual blooms on the plant.*—About 5–7 days depending on temperatures.
*Fragrance.*—Very slightly sweet.
*Color of peduncle.*—RHS 143B.
*Length of peduncle.*—9–13 cm.
*Width of peduncle.*—0.2 cm.
*Texture of peduncle.*—Glabrous, sparse short hirsute.
*Color of pedicel.*—RHS 143C.
*Length of pedicel.*—1.1–1.5 cm.
*Diameter of pedicel.*—0.1 cm.
*Texture of pedicel.*—Short hirsute.

Corolla:

*Form.*—Single, zygomorphic, 5-lobed, 3 petals, fused at the base and forming the fan-shaped upper lip; 2 petals completely fused, forming the somewhat reflexed lower lip; spurred.
*Length of flower.*—2.2–2.5 cm.
*Width of flower.*—2.1–2.3 cm.
*Depth of flower.*—0.5–0.6 cm.
*Nectar guide.*—Two stripes closely parallel, about 4 mm in length, the color is RHS 3C.
*Throat diameter.*—0.5–0.6 cm.
*Throat diameter at the base of flower.*—0.2–0.3 cm.
*Throat color.*—Very pale purple, RHS 76D for the upper part; RHS 76C to RHS 76D for the lower part (lower lip).
*Funnel length.*—0.2–0.3 cm.
*Funnel color.*—RHS 76D.
*Color upper petals, upper surface.*—RHS N81B, may fade to RHS N82B, nearly black veins, RHS 186A, may be visible.
*Color lower petals, upper surface.*—RHS N82B with a basal blotch of RHS 3C.
*Color all petals, lower surface.*—RHS 85A.
*Length of upper petals.*—1.2–1.4 cm.
*Width of upper petals.*—2.1–2.3 cm.
*Length of lower petals.*—1.0–1.2 cm.
*Width of lower petals.*—1.4–1.5 cm.
*Shape of upper petals.*—Obovate.
*Apex of upper petals.*—Rounded, the middle petal appears to be deeply divided.
*Base shape.*—Fused.
*Petal margin.*—Entire.
*Shape of lower petals.*—Completely fused and moulded.
*Apex of lower petals.*—Weakly rounded, wavy.
*Base.*—Fused.
*Margin.*—Entire, apart from one of two notches at the apex.
*Petal texture (upper and lower petals, upper surfaces).*—Papillose.
*Petal texture (lower surfaces).*—Smooth, glabrous.
*Color of spur.*—RHS 157A with RHS 155A at the tip.
*Length of spur.*—Most often 0.6 cm.
*Width of spur.*—0.1–0.2 cm.

Bud (just before opening):

*Color.*—RHS 77C to D.
*Length of bud.*—0.6–0.7 cm.
*Width of bud.*—0.4–0.5 cm.
*Shape.*—Initially roughly ovate, then flattens to 'oyster-shape' just before unfolding.
*Number of sepals.*—5.
*Color of sepals (upper and lower surfaces).*—RHS 143A with no anthocyanins.
*Length of sepals.*—0.25 cm.
*Width of sepals.*—0.15 cm.
*Sepal shape.*—Lanceolate to elliptical.
*Apex shape.*—Acute.
*Margins.*—Entire.
*Texture (outward surface).*—Densely pubescent; few glandular hairs.
*Texture (inner surface).*—Nearly glabrous.

Reproductive organs:

*Pistil.*—One.

*Length.*—0.3–0.4 cm.

*Style color.*—RHS 157D.

*Style length.*—0.1–0.2 cm.

*Stigma color.*—RHS 157A.

*Ovary.*—One, oval.

*Ovary color.*—RHS 143C.

*Number of stamen.*—4; 2 pairs with anthers coherent that are bowed or arching over and around the pistil.

*Color of filaments.*—RHS 155A or sometimes slightly RHS 157A.

*Length of filaments.*—One pair 0.4–0.5 cm and another pair 0.3 cm.

*Anther shape.*—Ovate.

*Anther diameter.*—1 mm.

*Anther color.*—RHS 13D.

*Pollen amount.*—Moderate.

*Pollen quantity.*—Moderate.

*Color of pollen.*—RHS 13C.

*Fertility/seed set.*—Not observed on this hybrid.

Disease/pest resistance: Disease resistance or susceptibility has not been observed on this hybrid.

What is claimed is:

1. A new and distinct variety of *Nemesia* plant named 'Cnem Bule', substantially as illustrated and described herein.

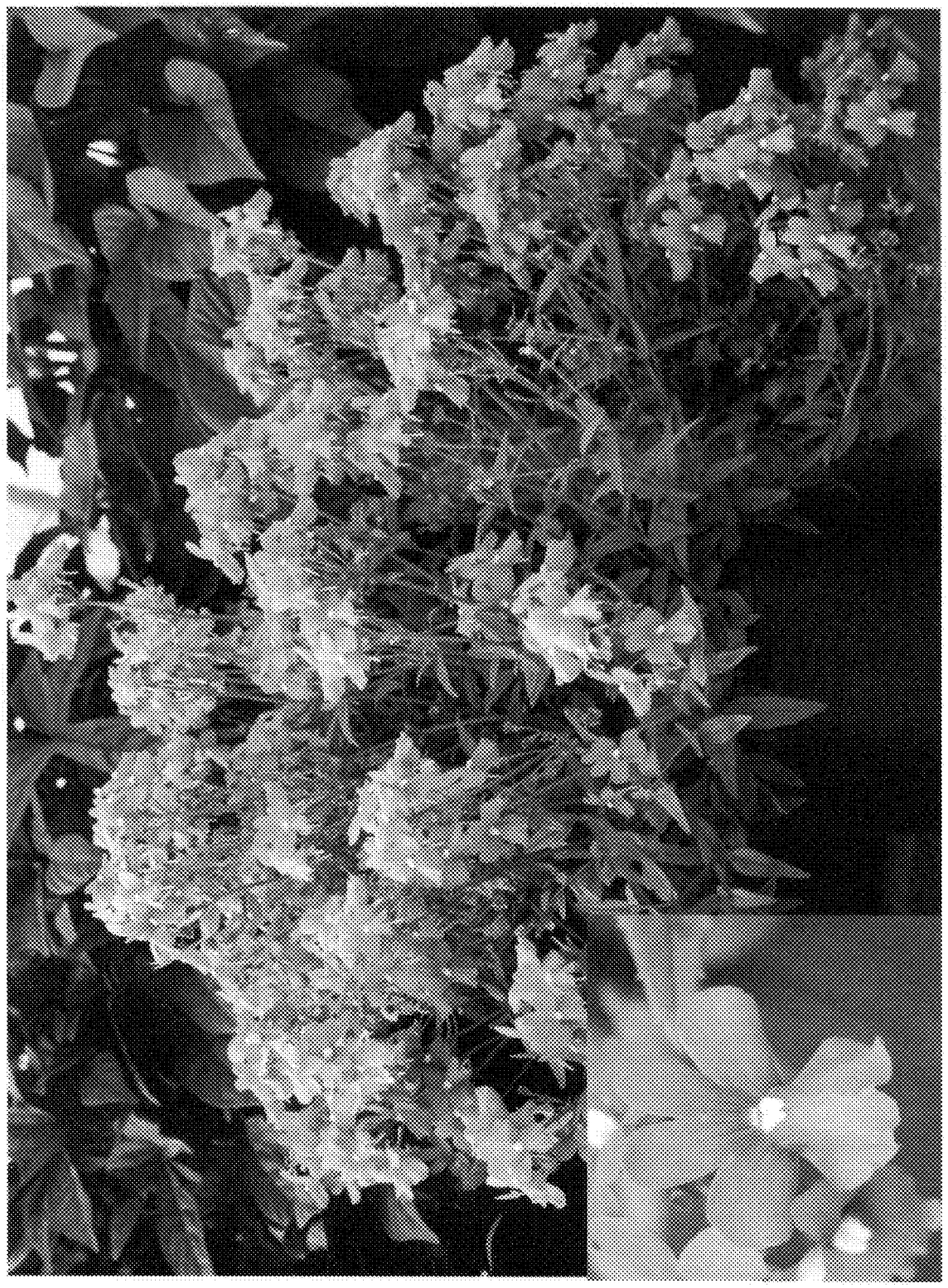

* * * * *